United States Patent [19]

Ueda et al.

[11] Patent Number: 5,242,915
[45] Date of Patent: Sep. 7, 1993

[54] FORMULATION USEFUL FOR THE INHIBITION OF MASSIVE RELEASE OF CEREBRAL GLUTAMATE

[75] Inventors: Motohiko Ueda, Suita; Takefumi Gemba, Amagasaki; Masami Eigyo, Ikoma; Ikuo Adachi, Suita, all of Japan

[73] Assignee: Shionogi & Co., Ltd., Osaka, Japan

[21] Appl. No.: 885,864

[22] Filed: May 20, 1992

[30] Foreign Application Priority Data

May 21, 1991 [JP] Japan .................................. 3-146820

[51] Int. Cl.$^5$ .......................................... A61K 31/395
[52] U.S. Cl. ................................................... 514/210
[58] Field of Search ......................................... 514/210

[56] References Cited

U.S. PATENT DOCUMENTS 4,703,051 10/1989 Adachi et al. .................... 514/291

OTHER PUBLICATIONS

Chem. Abst. 114-35719®(1991).
Scriabine et al., The FASEB Journal, vol. 3, May 1989 pp. 1799-1806.
Tollefson, Biol. Psychiatry, vol. 27, No. 10, May 15, 1990 pp. 1133-1142.
Masui et al., Drug Development Research, vol. 20, 1990 pp. 453-464.

Primary Examiner—S. J. Friedman
Attorney, Agent, or Firm—Wenderoth, Lind & Ponack

[57] ABSTRACT

A method useful for the treatment or prevention of diseases caused by a massive release of cerebral glutamate, in particular epilepsy and dementia, and pharmaceutical formulations therefor, which comprise, as an active ingredient, a therapeutically effective amount of methyl (+)-(4S)-4,7-dihydro-3-isobutyl-6-methyl-4-(3-nitrophenyl)thieno[2,3-b]pyridine-5-carboxylate (S-312-d).

4 Claims, 3 Drawing Sheets

FORMULATION USEFUL FOR THE INHIBITION OF MASSIVE RELEASE OF CEREBRAL GLUTAMATE

FIELD OF THE ART

The present invention relates to pharmaceutical formulations capable of inhibiting a massive release of cerebral glutamate, which comprise, as an active ingredient, methyl (4S)-4,7-dihydro-3-isobutyl-6-methyl-4-(3-nitrophenyl)thieno[2,3-b]pyridine-5-carboxylate, and a method for preventing and treating diseases caused by the massive release of cerebral glutamate. More specifically, it relates to pharmaceutical formulations useful for the treatment or prevention of epilepsy, dementia, or necrosis of cerebral cells.

BACKGROUND OF THE INVENTION

Recently, interest has been concentrated on various types of dementia such as cerebrovascular dementia, Altzheimer's disease, senile dementia, and the like, and the demand for effective methods for treating and preventing them are continuously increasing. It has been reported that a neurotoxic effect of cerebral excitatory amino acids, especially glutamate, which exhibits a neurotoxic effect following the binding to receptors, may be responsible for these diseases (Sinozaki, Gendaikagaku, 10: 38–44 (1987)). Prior to the present invention, many compounds had been provided with the intention of decreasing or eliminating the above aggravating effect of cerebral glutamate, including N-methyl-D-aspartic acid (hereinafter referred to as NMDA) channel antagonist such as MK-801 (H. Kato et al., Brain Res. 516: 175–179 (1990)]. However, they are not clinically applicable because of serious toxic effects. Therefore, safe compounds capable of preventing the massive release of cerebral glutamate have been required.

In the course of an investigation into dihydropyridine derivatives for the purpose of developing substances having Ca-blocking activity, a series of 4-aryl-4,7-dihydrothieno[2,3-b]pyridine-5-carboxylate derivatives were synthesized and tested for the binding affinity to $Ca^{++}$ channels, coronary vasodilating effect and antihypertensive activity, and methyl 4,7-dihydro-3-isobutyl-6-methyl-4-(3-nitrophenyl)thieno[2,3-b]pyridine-5-carboxylate (hereinafter, referred to as S-312) was found to be a potent vasodilating agent and also proved to have a potent antihypertensive and coronary vasodilating effect with lesser adverse reactions (U.S. Pat. No.4,703,051). Further study revealed that the major biological activities of said compound resides in the (+)-enantiomer with S configuration, i.e., methyl (+)-(4S)-4,7-dihydro-3-isobutyl-6-methyl-4-(3-nitrophenyl)thieno[2,3-b]pyridine-5-carboxylate (hereinafter, referred to as S-312-d), whose preparation is described in the Japanese Patent Publication (KOKAI) No.52890/1992.

Because of their selective Ca-blocking effect on vascular smooth muscle, S-312-d and S-312 exhibit antihypertensive activity, as well as peripheral, cerebral, and coronary vasodilating actions, which makes them useful in the treatment of circulatory diseases such as angina pectoris, hypertension, cerebrovascular dysfunction, arrhythmia, or the like. The useful effect on various cerebrovascular diseases is however not attributable to any specific properties of these compounds, but to the cerebral vasodilating effect common to Ca-blockers. Though one of ordinarily skill in the art might have thought that Ca-blockers were effective for preventing the cerebral apoplexy from occurring based upon their vasodilating action, he could hardly expect before the present invention that S-312-d was so effective on the ischemic neuronal cell damages consequent upon the cerebral apoplexy as well as the senile dementia.

DISCLOSURE OF THE INVENTION

The present invention provides a pharmaceutical formulation useful in the prevention or treatment of various diseases caused by a massive release of cerebral glutamate. Examples of such diseases include epilepsy, senile dementia, Huntington's chorea, neuronal cell damage following ischemia, and the like. The details of the invention will be hereinafter described.

The present invention was established by the finding that S-312-d has an ability of inhibiting specifically a massive release of cerebral glutamate from hippocampus, which phenomenon is often observed during cerebral ischemia. Further, S-312-d was proved to have a potent inhibitory effect on a convulsion induced by sound stimulation in DBA/2 mice but not on those induced by NMDA or pentylenetetrazol.

The effect of S-312-d on the massive release of cerebral glutamate was investigated using stroke-prone spontaneously Hypertensive Rats (hereinafter, referred to as SHRSP). Thus, an experimental cerebral ischemia was caused in SHRSPs by the occlusion of both common carotid arteries (hereinafter, referred to as BCAO). During the ischemic period, a massive release of glutamate in hippocampal CAI region was observed (see, FIG. 1). S-312-d and the other dihydropydine $Ca^{++}$ antagonists (nimodipine, nilvadipine) were then evaluated for inhibitory effect on the ischemic glutamate release in hippocampal CAI region, resulting in that only S-312-d was significantly effective (see, FIG. 2). It is noteworthy that S-312-d inhibits exclusively the ischemic glutamate release but not the normal resting release.

According to the recent reports, cerebrovascular dementia, Altzheimer's disease, Huntington's disease, and the like are probably associated to neurotoxic effects of cerebral excitatory amino acids, typically glutamate. There are some proposals as to the mechanisms by which glutamate exerts its neurotoxic effect.

Cotman, C. W. and Iversen, L. L. (TINS, 10: 263–265 (1987)) suggested that the amino acid-release causes an over excitement of NMDA receptor, a subtype of glutamate receptor, which leads to a progressive pathological change and the death of neuronal cells.

According to the proposal of Nagasawa and Kogure ("IGAKU-NO-AYUMI", vol. 158, pp.613–618, Aug. 31, 1991)), the cause of a delayed necrosis of neuronal cells can be explained as follows: when cerebral cells are faced with an ischemic condition, (a massive calcium influx takes place following the ischemic depolarization of neuronal cell membrane), and which leads to the delayed cellular necrosis.

As can be seen from the experimental results shown in Table 2, S-312-d possesses an ability of preventing the delayed necrosis of neuronal cells following ischemia and is useful for protecting cranial nerve neuronal cells from damage. Thus, S-312-d also possesses an ability of protecting cerebroneuronal cells of those in danger of being exposed to cerebral ischemia by, for example, placed under a hypoxic and/or undernutritional conditions, as well as treating or preventing dementia.

Thus, the present invention provides a pharmaceutical formulations for the prevention and/or treatment of dementia, which comprises, as an active ingredient, a therapeutically effective amount of S-312-d.

Martin, J. B. and Gusella, J. F. (N. Engl. J. Med., 315: 1267-1276 (1986)) suggested that baclofen can decrease the excitation level of neuronal cells excited by glutamate through the activation of suppressive neuronal cells, whose transmitter is Y-amino butyric acids, thereby preventing progress of Huntington's chorea disease effectively. Baclofen, however, proved to inhibit the normal glutamate release but not the ischemic release.

On the contrary, S-312-d is exclusively effective on ischemic glutamate release, and therefor can be used clinically in the prevention and/or treatment of disorders or symptoms caused by massive release of cerebral glutamate. Examples of diseases which can be treated with S-312-d include convulsion, epilepsy, diseases caused by massive release of cerebral glutamate such as vascular dementia, Altzheimer's disease, Huntington's chorea and senile dementia, and necrosis of neuronal cells due to various causes other than the cerebral glutamate.

As mentioned in the above, S-312-d inhibits sound-induced convulsion in DBA/2 mouse. Although the mechanism by which the convulsion is induced in DBA/2 mouse is not clear, it may be caused by the activation of NMDA receptors with released glutamate (De Sarro, G. B. et al., Br. J. Pharmacol. 93: 247-256 (1988)).

Croucher, M. J. et al.( Neuropharmacology, 23: 467-472 (1983)) reported that because NMDA receptor antagonist inhibited said convulsion, the similar mechanism as the above can be also responsible for the reflection-induced epilepsy in DBA/2 mouse.

The above-mentioned facts, that is, S-312-2 can inhibit the both of a) the sound-induced convulsion, and b) the massive release of cerebral glutamate, indicate that S-312-d is also useful as an antiepileptic.

Thus, the present invention also provides an antiepileptic formulation which comprises, as an active ingredient, a therapeutically effective amount of S-312-d.

As previously described, S-312-d is a known compound which can be prepared using any of known methods, for example, through a resolution of a racemic S-312 which can be obtained according to the procedures described in U.S. Pat. No. 4,703,051. However, it is preferably prepared using the method disclosed in the Japanese Patent Publication (KOKAI No.52890/1992) using, as a starting material, 2-t-butyl 5-methyl 4,7-dihydro-3-isobutyl-6-methyl-4-(3-nitrophenyl)thieno[2,3-b]pyridine-2,5-dicarboxylate which is disclosed in Japanese Patent Publication (KOKAI) No.10087/1987. The above-mentioned references are herein incorporated by reference.

S-312-d can be orally or parenterally administered to human or animals and can be formulated into various forms in compliance with the usage, including tablets, capsules, pills, granules, fine granules, aqueous solutions, emulsions, vaginal suppository, suppository, or the like. Formulations of the invention can be prepared using any of the known methods in the art employing conventional carriers or excipients therefor such as lactose, sucrose, starch, cellulose, talc, stearic acid, magnesium stearate, magnesium oxide, calcium sulfate, powdered gum arabic, gelatin, sodium alginate, sodium benzoate, and the like. Solutions, suspensions or injectable solutions are also employable by dissolving S-312-d together with a solubilizing agent, into distilled water, saline, Ringer's solution, or the like, or suspending it in, for example, sesame oil.

The dose of S-312-d may vary depending on various factors such as purpose and/or method of treatment, administration route, conditions of the patient to be treated, and the like. However, it may be administered to an adult at a dose of about 0.1-100 mg/day, preferably about 0.5-50 mg/day, more preferably about 1-10 mg/day.

PREPARATION 1

Figure 1:
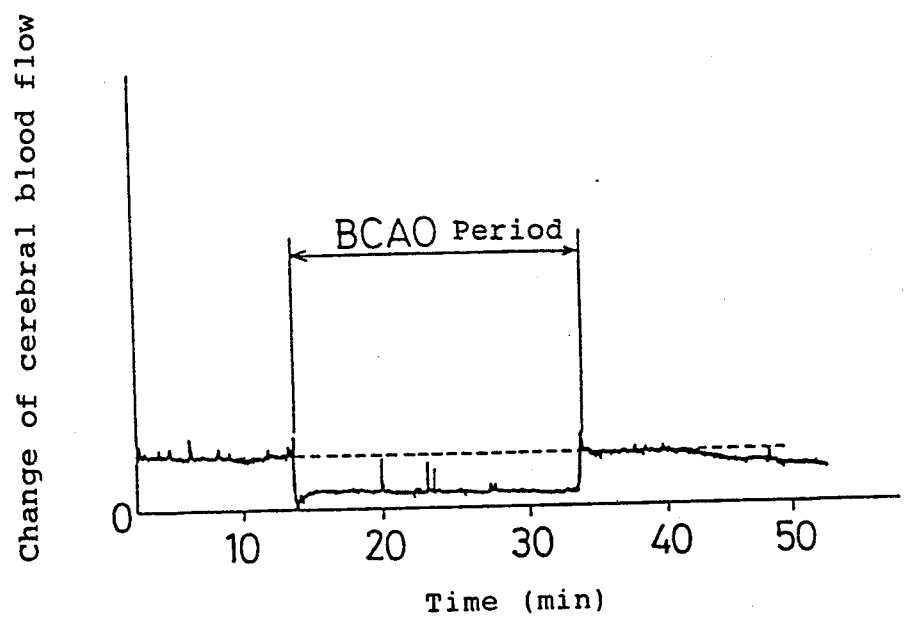
FIG. 1 shows the change of regional (at hippocampal CIA) cerebral blood flow in SHRSP before, during, and after ischemia caused by BCAO. The relative changes in blood flow is plotted on the ordinate, and the time (min) on the abscissa.

Methyl(+)-(4S)-4,7-dihydro-3-isobutyl-6-methyl-4-(3-nitrophenyl)thieno[2,3-b]pyridine-5-carboxylate (S-312-d)

1.
4,7-Dihydro-3-isobutyl-5-methoxycarbonyl-6-methyl-4-(3-nitrophenyl)thieno[2,3-b]pyridine-2-carboxylic acid To a mixture of 108.8 g (0.224 mol) of 2-t-butyl 5-methyl 4,7-dihydro-3-isobutyl-6-methyl-4-(3-nitrophenyl) thieno[2,3-b]pyridine-2,5-dicarboxylate, 67.0 g (0.447 mol) of sodium iodide in acetone 500 ml was added dropwise 48.6 g (0.447 mol) of trimethylsilyl chloride at room temperature under stirring and the mixture stirred for another 5 hr at room temperature.

To the mixture was then added dropwise 1,110 ml of ice-cold water, and 50 ml of 10% $Na_2S_2O_3$ solution, successively. The crystalline precipitates are separated by filtration, washed with water, and dried to yield 98.4 g (yield 98.2%; purity on the basis of HPLC, about 96.1%) of the titled 2-carboxylic acid as yellowish crystals, mp. 173°-174° C.

IR (Nujol) max: 3306(NH), 2596(COOH), 1649(CO), 1342($NO_2$) $cm^{-1}$ $^1$H-NMR ($d_6$DMSO) δ:0.75(3H,d,j=7Hz), 0.85(3H,d,j=7Hz), 1.69(1H,m), 2.13(1H,dd,j=7.11Hz), 2.30(3H,s), 2.88(1H,dd,j=7,13Hz), 3.57(3H,s), 5.21(1H,s), 7.53-8.08(4H,m)

Elementary Analysis for $C_{21}H_{22}N_2O_6S$: Theory: C, 58.59; H, 5.15; N, 6.51 Found : C, 58.29; H, 5.16; N, 6.40°. HPLC: $t_R$4.8 min (column: TSK-GEL ODS-120T, 5 μm (4.0×250 mm); mobile phase: methanol, 0.5 ml/min; detection: UV254 nm; 35 atmospheric pressure.

2. Methyl (+)-(4S)-4,7-dihydro-3-isobutyl-6-methyl-4-(3-nitrophenyl)thieno[2,8-b]pyridine-5-carboxylate (S-312-d)

2.1. Cinchonine salt of S-312-d

A mixture of 97.1 g (0.224 mol) of 2-carboxylic acid obtained in the above 1 and 65.9 g (0.224 mol) of cinchonine in 500 ml of ethanol was heated under reflux for 10 min to dissolve the reaction materials and the solution allowed to stand for 20 min at room temperature. The crystalline precipitates are filtered, washed with ethanol, and dried to yield 69.2 g (yield=42.8%) of S-312-d in the form of cinchonine-addition salt as yellowish crystals, mp. 224°–226° C. (decomp.).

$[\alpha]^{23}_D$: +394.4°±8.5° (C=0.513,DMSO)

IR (Nujol) max: 3226(NH), 1668(CO), 1342(NO$_2$) cm$^{-1}$.

2.2. S-312-d

To a solution of 64.4 g (0.089 mol) of cinchonine salt obtained in the above 2.1. in 320 ml of methanol was added dropwise 14 ml (0.27 mol) of sulfuric acid with stirring. The temperature of the reaction mixture was then elevated gradually and the mixture refluxed for 15 min. To the cooled mixture was then added 650 ml of ice-cold water and the crystalline precipitates were filtered, washed with water, and dried to yield 47.5 g (yield=93%) of S-312-d as yellowish crystals in the form of flat plates, mp =173°–175° C.

$[\alpha]^{23}_D$: +274.3°±3.0° (C=1.019, EtOH).

Elementary Analysis for $C_{20}H_{22}N_2O_4S$: Theory: C, 62.16; H, 5.74; N, 7.25 Found : C, 62.04; H, 5.67; N, 7.28

IR(Nujol) max: 3305(NH), 1630(C=O), 1342 (NO$_2$) cm$^{-1}$  $^1$H-NMR (CDCl$_3$)δ: 0.72(3H,d,j=6Hz), 0.88(3H,d,j=6Hz), 1.60(1H,m), 2.02(1H,dd,j=7,15Hz), 2.13(1H,dd,j=7,15Hz), 2.37(3H,s), 3.63(3H,s), 5.25(1H,s), 6.22(1H,s), 7.35–8.08(4H,m).

HPLC: $t_R$ 15.5 min (column: SUMIPAX OA2000, 5 μm (4.0×250 mm); mobile phase: hexane-isopropanol (9:1), 1.0 ml/min; detection: UV248 nm; 40 atmospheric pressure.

The following experiments were conducted to evaluate the biological activity of S-312-d.

Experiment 1

Effect of S-312-d on the Ischemic Release of Glutamate in Hippocampal CAI Region Test compound: S-312-d Reference compound: nilvadipine, and nimodipine
Animal: Five male SHRSP bred at the Aburahi Laboratories (Shionogi) at ten to twelve weeks of age were used in a group. Animals were fed CA-1 (Nihon Clea) and tap water ad libitum.

A. Explanation of Occlusion of both Common Carotid Arteries (BCAO)

A.1. Method

Hippocampus CAI region was made ischemia by the occlusion of both common carotid arteries (BCAO) into rats as follows:

Rats were anesthetized with halothane (3%) and the cervical region proximal to abdomen was incised to expose the common carotid arteries. Both arteries were occluded with nylon threads with each end exposed at the back of the neck through either of two holes of a tube (double lumen PE tube, Natsume Seisakusho, & Co.). Occlusion was induced in the both common carotid arteries by pulling strongly each exposed end of threads. BCAO was stopped by gradually pulling down the each end of threads passed under arteries proximal to abdomen. During the ischemic period, the halothane inhalation was stopped.

A.2. Determination of Regional Cerebral Blood Flow

The determination of the regional cerebral blood flow was conducted using a laser doppler tissue flow meter (LFA-2, Biomedical Science, Japan) with a needle-type sensor (450 μm in diameter) inserted into the hippocampal CA1 region opposite to the site where a microdialysis probe had been fixed. The blood flow during BCAO was estimated as almost negligible on the assumption that the blood flow after the death of rat is "0".

B. Effect of S-312-d on the Ischemic Release of Cerebral Glutamate

B.1. Administration of Test Compounds

S-312-d (0.3 mg/kg), nilvadipine (3 mg/kg), or nimodipine (3 mg/kg) was dissolved into polyethylene glycol 400 and administered into duodenum in each rat at 40 min before BCAO.

B.2. Measurement of Glutamate Release by Microdialysis

Under the anesthesia with halothane (1–2%), rats were fixed on cerebral stereotaxic frame and equipped with an artificial respirator (1 cc/100 gbw×60 times/min), while being maintained at 37 ° C by settling a heating pad beneath the lower abdominal region. A hole was drilled on the exposed skull and a microdialysis probe (CMA/10, membrane length 2 mm, BAS, Sweden) was inserted gently. Measurement was started after 3 hr from the surgery in order to avoid the influence of tissue damage. The probe was perfused with Ringer's solution at a flow rate of 2 μl/min by a microdialysis pump (CMA/100, BAS, Sweden). The dialysates were collected for each 5-min perfusion and pooled. Sampling was started at 10 min before the BCAO. BCAO was continued for 20 min when it was stopped by loosening (occluding) threads to allow cerebral circulation. The sampling was continued for 20 min after the discontinuation of the BCAO. Samples were then subjected to quantitative analysis for glutamate without further treatments.

B.3. Determination of Glutamate Concentration

The concentration of glutamate was determined by HPLC substantial in accordance with the HPLC-ECD method of Donzanti et al. (Life Sci. 43: 913 (1988)) The glutamate-containing sample was reacted with o-phthlaldehyde/β-mercaptoethanol solution for 2 min and injected into a reverse-phase column and eluted under the following conditions. The eluate was then analyzed for the presence of glutamate by an electrochemical measurement of oxidation-reduction current.

Conditions for the Measurements

Column: C 18, particle size: 3 μm, 8 cm×4.6 mm
Temperature: 39° C.
Mobile phase: a mixture of 0.1M phosphate buffer (pH 6.4), 0.13 mM Na$_2$EDTA, and 22% MeOH
Flow rate: 1 ml/min

Results

Figure 2:
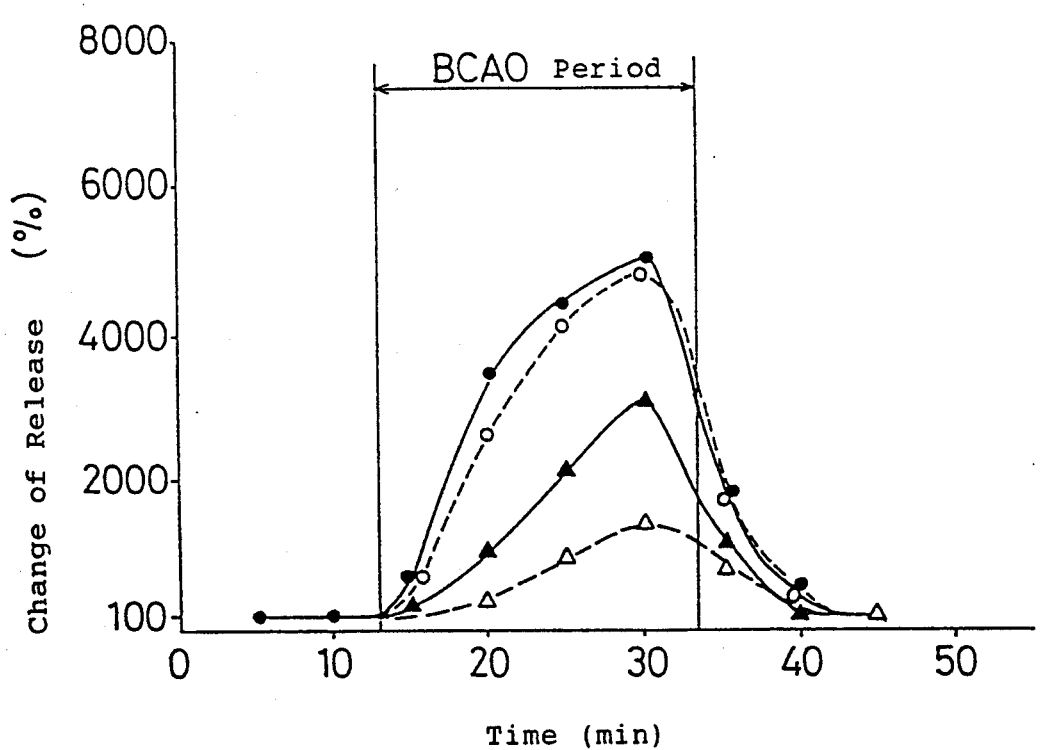
FIG. 2 shows the effect of Nimodipine (closed circle), Nilvadipine (closed triangle), S-312-d (open triangle), and absence of Ca-blocker (closed triangle), on the massive release of cerebral glutamate during ischemia. In the figure, % changes of the glutamate release to the resting release is plotted on the ordinate, and the time (min) on the axis.

Results are shown in FIGS. 1 and 2.

FIG. 1 shows the regional blood flow before, during and after the ischemic period caused by BCAO. In the figure, the relative changes in regional cerebral blood flow are plotted on the ordinate, and the time (min) on the axis. As can be seen from the FIG. 1, the regional blood flow decreased to an undetectable level during ischemic period and is recovered to the pre-ischemic level after the reperfusion.

FIG. 2 shows the influence of S-312-d on the massive release of cerebral glutamate during BCAO. In the figure, the % change of the release of glutamate to its basal release is plotted on the ordinate, and the time (min) on the abscissa. As is clear from the FIG. 1, S-312-d inhibited the massive release of glutamate during BCAO without affecting the normal resting release of glutamate. On the contrary, neither nilvadipine nor nimodipine shows significant effect on the glutamate release during BCAO.

Thus, S-312-d inhibits specifically the massive release of glutamate during cerebral ischemia but not the normal cerebral release of glutamate in contrast to baclofen which inhibits the normal release but not the ischemic release. From this evidence, one can expect that S-312-d is clinically useful and can be applied widely to the massive release of cerebral glutamate which results from many causes, in addition to ischemia, such as overexcitation of neurons during convulsion.

Experiment 2

Effects of S-312-d on the Ultrasonically-induced Convulsion in DBA/2 Mouse

Test compound: S-312-d

Reference compound: methyl (−)-(4R)-4,7-dihydro-3-isobutyl-6-methyl-4-(3-nitrophenyl)thieno[2,3-b]pyridine-5-carboxylate (hereinafter, referred to as S-312-1, an optical isomer of S-312-d), Nicardipine, Nimodipine, and Flunarizine.

Animal: Ten mice consisting of five each of male and female DBA/2 mice (weighing from 7 to 11 g) bred at the Aburahi Laboratories (Shionogi) at three weeks of age were used in a group.

Method

One hour before the ultrasonic treatment, each mouse of test group orally received S-312-d as a solution in polyethylene glycol 400. To each mouse of control groups was orally administered either of Nicardipine, as a solution in polyethylene glycol 400, S-312-1, Nimodipine or Flunarizine, as a suspension in gum arabic. Convulsion was induced in mouse by an ultrasonic treatment (70–90 db, 1 min) and the number of tetanic death was observed. ED50 value of anti-convulsant effect of each compound was calculated by probit method using the death from trauma as an indication.

Results

Figure 3:
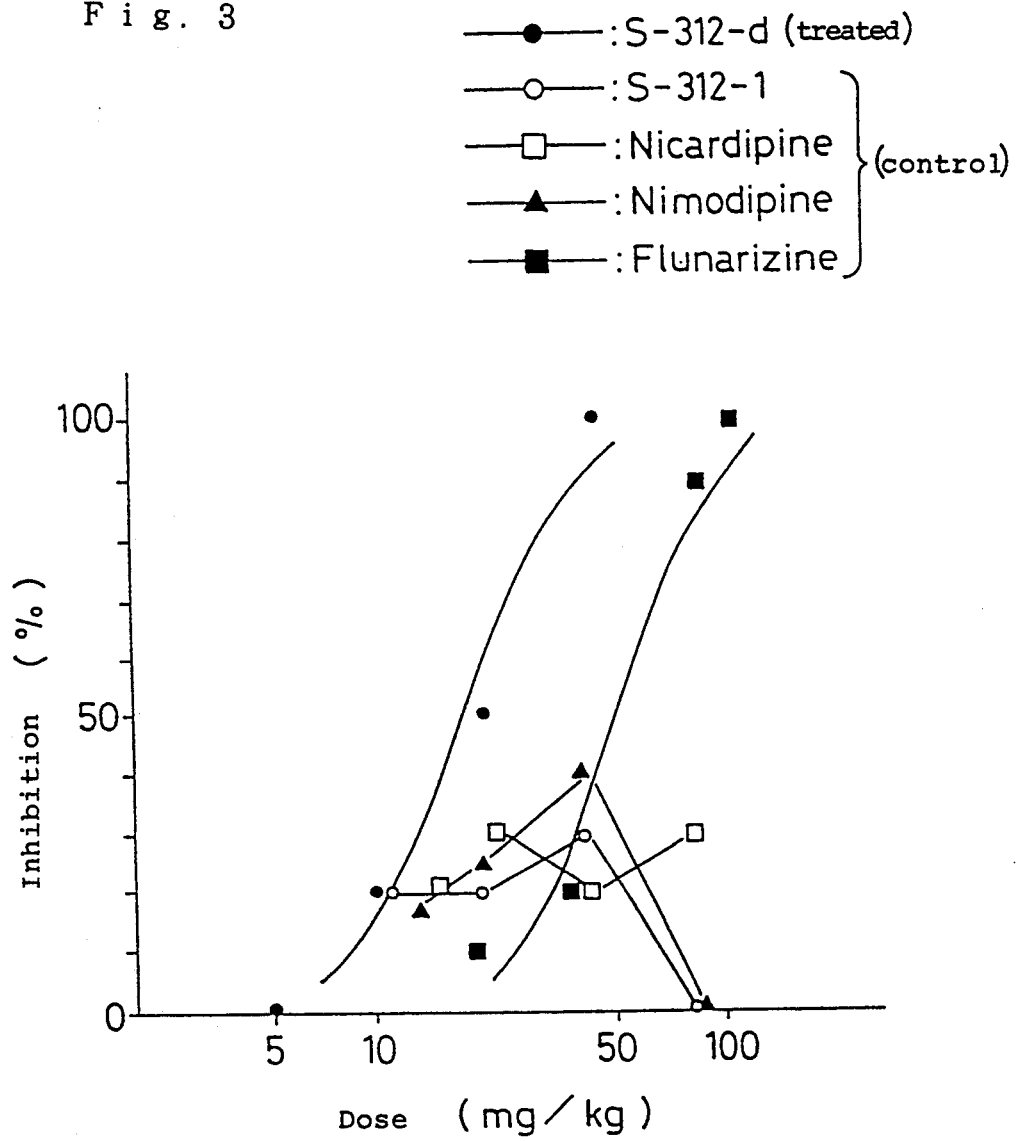
FIG. 3 shows the effect of S-312-d( closed circle), S-312-1 (open circle), Nicardipine (open square), Nimodipine (closed triangle), Flunarizine (closed square) against the ultrasonically-induced lethal convulsion in DBA/2 mouse. The inhibitory rate (%) is plotted on the ordinate, and the dose (mg/kg) on the abscissa.

Results are shown in FIG. 3 and in Table 1 below. As is clear from the FIG. 1 and Table 1, S-312-d and Flunarizine show the dose-dependent anti-convulsant effect, while remaining typical dihydropyridine Ca-blockers, i.e., Nicardipine, Nimodipine and S-312-1, show anticonvulsive effect of less than 40%. It is notable that the maximum effects of Nicardipine and Nimodipine are 30% and 40%, respectively, at a dosage ranging from 20–80 mg/kg, and that of S-312-1 is 30% at a dosage ranging from 10–80 mg/kg.

TABLE 1

| Group | Compound | ED50 (mg/kg) |
|---|---|---|
| Treated | S-312-d | 17.6 |
| Control | S-312-1 | 30% at 10–80 mg/kg |
| | Nicardipine | 30% at 20–80 mg/kg |
| | Nimodipine | 40% at 20–80 mg/kg |
| | Flunarizine | 48.1 |

Anticonvulsive Effect in DBA/2 Mouse

Experiment 3

Effects of S-312-d on the Delayed Neuronal Death During Cerebral Ischemia

Test compound: S-312-d

Animal: eight to twelve (n=8–12) male SHRSP bred at the Aburahi Laboratories (Shionogi) were used in a group. Animals were fed CA-1 (Nihon Clea) and tap water ad libitum.

Method

S-312-d was dissolved into polyethylene glycol 400 solution and intraperitoneally administered to a SHRSP at 60 min before the introduction of a global cerebral ischemia. Cerebral ischemia was then caused in each rat for 20 min and stopped to allow cerebral circulation in the same manner as the above Experiment 1. For the histological observation on the delayed neuronal death, a fixation of tissue was conducted by perfusing the animal from the left ventricle using 4% paraformaldehyde at a flow rate of 10 ml/min by means of perista pump (AC-2110, ATTA) on the 7th day from the ischemia. After the removal of brain, cerebral region containing hippocampus was embedded in paraffin, from which sliced preparations of 4 μm thick were prepared. Each cerebral preparation was stained with hematoxylin-eosin and the density of the living pyramidal neurons (n/mm) was determined by counting the number of neurons per 1 mm length of the hippocampal CAI region under a light microscope. The data were expressed as the mean ±S.E.M. For the purpose of comparison, SHRSPs with or without ischemic maneuvering were both treated with propylene glycol, in exactly the same manner as the above. Results are shown in Table 2 below.

TABLE 2

| Group | <40 | 40–80 | 80–120 | >120 | mean ± S.E.M |
|---|---|---|---|---|---|
| Normal | 0 | 0 | 1 | 7 | 160 ± 9 |
| Control | 2 | 4 | 6 | 0 | 69 ± 10* |
| Treated | | | | | |
| (I) | 3 | 4 | 2 | 3 | 73 ± 12** |
| (II) | 2 | 1 | 4 | 6 | 114 ± 17*** |

Density of Neurons (n/mm)

Normal group (n = 8), control group (n = 12), treated group (I) (n = 12, S-312-d 0.01 mg/kg) and treated group (II) (n = 13, S-312-d at the dosage of 0.1 mg/kg)
*p < 0.05,
**p < 0.01; significantly different from normal group.
***p < 0.01; significantly different from control group.

As can be seen from the above Table 2, there is a marked neuronal necrosis in the control group compared with the normal group. It is also clear from the table that the pretreatment with S-312-d is significantly effective for the protection of cerebral neurons against ischemic necrosis of cells.

Experiment 4

Single Dose Toxicity

A 5% Gum Arabic suspension of S-312-d was orally administered to 6-week-old Jcl:SD male rats (n =6) at a S-312-d dosage of 5000 mg/kg each. During a 14 day observation, they were all alive.

The following formulation examples are illustrative only and are not intended to limit the scope of the invention.

EXAMPLE 1

Powders are prepared using the following ingredients:

|  | Quantity (mg) |
| --- | --- |
| S-312-d | 4 |
| Corn starch | 93 |
| St—Mg* | 1 |
| Talc | 1 |
| Kp80** | 1 |
| Total | 100 mg |

*St—Mg = magnesium stearate
**Kp80 = Carplex 80# (Shionogi Seiyaku Kabusiki Kaisha, Japan)

The above ingredients are mixed thoroughly.

EXAMPLE 2

Hard gelatin capsules are prepared using the following ingredients:

|  | Quantity (mg) |
| --- | --- |
| S-312-d | 4 |
| Corn starch | 93 |
| St—Mg | 1 |
| Talc | 1 |
| Kp80 | 1 |
| Total | 100 mg |

The above ingredients are mixed thoroughly filled into hard gelatin capsules in 100 mg quantities.

EXAMPLE 3

Tablets are prepared using the following ingredients:

|  | Quantity (mg/tablet) |
| --- | --- |
| S-312-d | 4 |
| Lactose | 56 |
| Corn starch | 28 |
| HPC* | 1.5 |
| CMC—Ca** | 10 |
| St—Mg | 0.5 |
| Total | 100 mg |

*HPC = hydroxypropyl cellulose
**CMC—Ca = calcium carboxymethyl cellulose

The above ingredients are mixed thoroughly and the resultant powders are compressed on tablet machine to yield tablets each weighing 100 mg.

What is claimed is:

1. A method for treating a disease accompanied by or caused by a massive release of cerebral glutamate, which comprises administering a therapeutically effective amount of methyl (+)-(4S)-4,7-dihydro-3-isobutyl-6-methyl-4-(3-nitrophenyl)thieno[2,3-b]pyridine-5-carboxylate to a patient in need of such treatment.

2. The method as claimed in claim 1, wherein the disease is epilepsy.

3. The method as claimed in claim 1, wherein the disease is dementia.

4. The method as claimed in claim 1, wherein the disease is of ischemic neuronal cell damages.

* * * * *